United States Patent
Karama et al.

(10) Patent No.: US 9,498,460 B1
(45) Date of Patent: *Nov. 22, 2016

(54) HALOGENATED TETRACYCLIC COMPOUNDS

(71) Applicant: KING SAUD UNIVERSITY, Riyadh (SA)

(72) Inventors: Usama Sayed Eisa Karama, Riyadh (SA); Mujeeb Abdullah Saeed Sultan, Riyadh (SA); Abdulrahman Ibrahim Almansour, Riyadh (SA); Kamal Eldin Hussein El Tahir, Riyadh (SA); Yasser Abbas Elnakady, Riyadh (SA); Talal Abdul Aziz Mohaya, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/092,597

(22) Filed: Apr. 6, 2016

(51) Int. Cl.
| | |
|---|---|
| *A61K 31/235* | (2006.01) |
| *A61K 31/11* | (2006.01) |
| *A61K 31/135* | (2006.01) |
| *A61K 31/045* | (2006.01) |
| *C07C 211/31* | (2006.01) |
| *C07C 47/24* | (2006.01) |

(52) U.S. Cl.
CPC ........... *A61K 31/235* (2013.01); *A61K 31/045* (2013.01); *A61K 31/11* (2013.01); *A61K 31/135* (2013.01); *C07C 47/24* (2013.01); *C07C 211/31* (2013.01)

(58) Field of Classification Search
CPC . C07C 211/31; C07C 47/445; C07C 47/447; C07C 47/23; C07C 47/24; A61K 31/11; A61K 31/137
See application file for complete search history.

(56) References Cited

U.S. PATENT DOCUMENTS

| 2,938,049 A | 5/1960 | Johnson at al. |
| 5,004,755 A | 4/1991 | Storni et al. |
| 9,125,866 B1 | 9/2015 | Karama et al. |

FOREIGN PATENT DOCUMENTS

| CA | 2304879 | 9/1998 |
| CA | 2304879 A1 * | 3/2000 |

OTHER PUBLICATIONS

Schofield et al., "Halogen Bonding (X-bonding): A Biological Perspective," Protein Science, 2012, vol. 22, pp. 139-152.
Xu et al., "Halogen Bond: Its role Beyond drug-Target Binding Affinity for Drug Discovery and Development," J. chem. Int. Model., 2014, vol. 54, pp. 69-78.

* cited by examiner

*Primary Examiner* — Paul A Zucker
(74) *Attorney, Agent, or Firm* — Richard C. Litman

(57) ABSTRACT

The anti-cancer compounds are represented by Formula I:

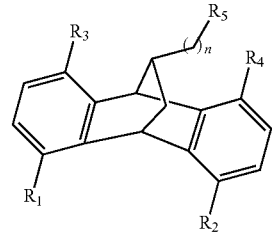

Formula I wherein $R_1$ and $R_2$ are either both hydrogen or both halogen, and if $R_1$ and $R_2$ are both hydrogen, $R_3$ and $R_4$ are both halogen, otherwise both $R_3$ and $R_4$ are hydrogen; wherein $R_5$ is CHO or $NHCH_3$; and wherein n is 0 to 3; provided that n is 0 only when $R_5$ is CHO, or a pharmaceutically acceptable salt or isomer thereof.

10 Claims, 1 Drawing Sheet

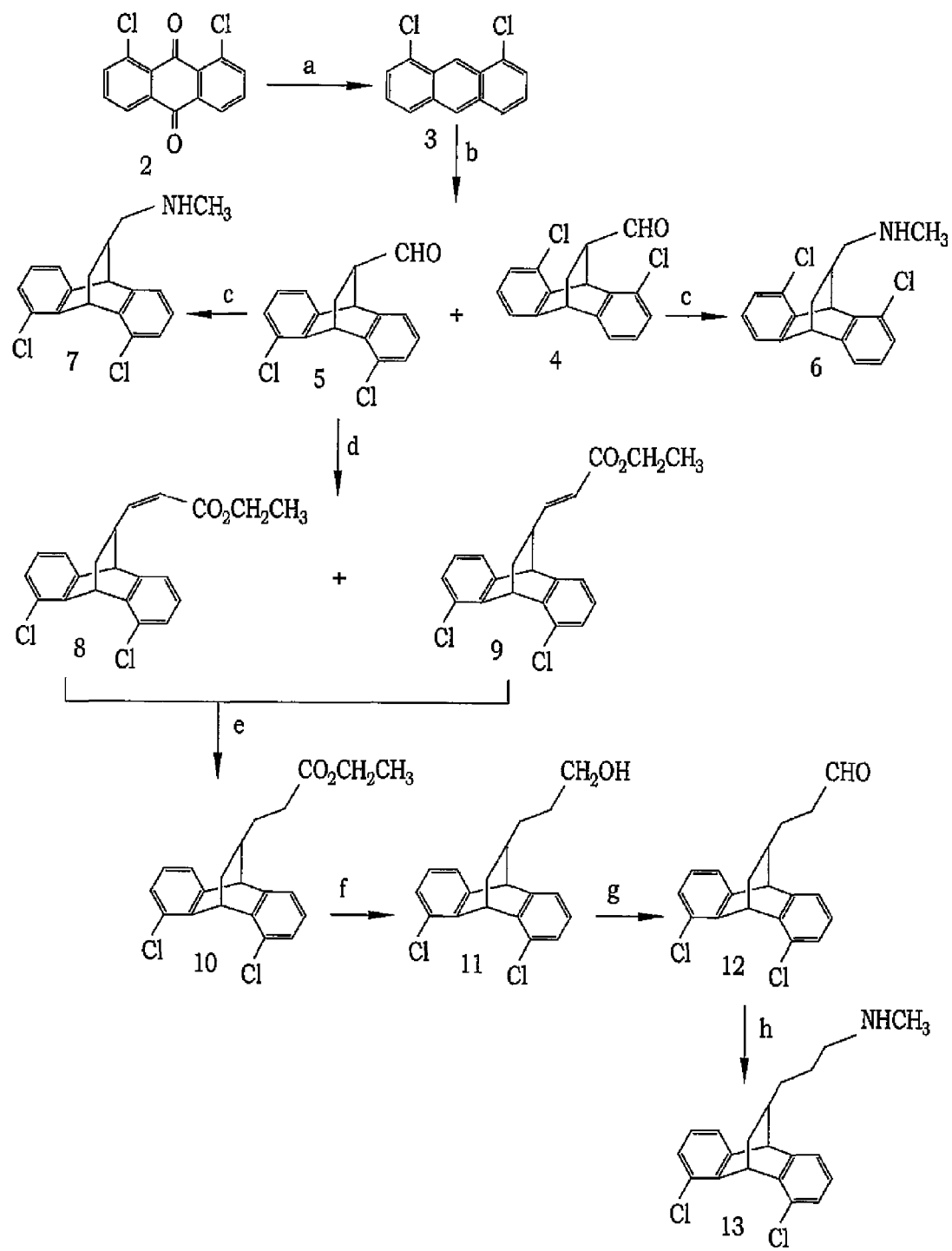

HALOGENATED TETRACYCLIC COMPOUNDS

BACKGROUND OF THE INVENTION

1. Field of the Invention

The present invention relates to halogenated tetracyclic compounds, and particularly to halogenated tetracyclic compounds useful as anti-cancer agents.

2. Description of the Related Art

Halogen bonds have attracted a great deal of attention in the past for hit-to-lead-to-candidate optimization for improving drug-target binding affinity, designing ligands to increase lipophilicity to facilitate the blood-brain barrier crossing, and to prolong the lifetime of the drug, thereby improving bioavailability. Halogenated compounds are important inhibitors against proteins, including those that are involved in carcinogenesis. It has been reported that about 50% of compounds in high-throughput drug screening contain halogens.

The tetracyclic antidepressant drug maprotiline 9,10-dihydro-N-methyl-9,10-ethanoanthracene-9-propanamine has recently been identified as a novel in vitro antiproliferative agent against Burkitts Lymphoma (BL) cell lines DG-75, which does not involve caspases, DNA fragmentation or PARP cleavage. This drug induced anti-multi-drug resistance (MDR) effects in both cancer cell lines and the malaria strain *plasmodium falciparum*. Thus, this compound holds potential in diverse therapeutic applications.

Antidepressant compounds that are dichlorinated compounds of the dihydroethanoanthracene family are disclosed in U.S. Pat. No. 9,125,866 B1, which is hereby incorporated herein by reference in its entirety.

Thus, halogenated tetracyclic compounds solving the aforementioned problems is desired.

SUMMARY OF THE INVENTION

According to one aspect, there is provided novel ethanoanthracene compounds represented by Formula I:

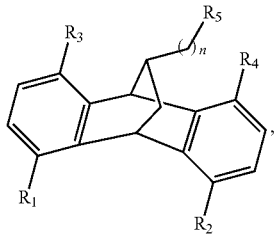

wherein $R_1$ and $R_2$ are either both hydrogen or both halogen, and if $R_1$ and $R_2$ are both hydrogen, $R_3$ and $R_4$ are both halogen (particularly chlorine), otherwise both $R_3$ and $R_4$ are hydrogen;

wherein $R_5$ is CHO or $NHCH_3$;

wherein n is 0 to 3;

provided that n is 0 only when $R_5$ is CHO or a pharmaceutically acceptable salt thereof or isomers thereof.

The compounds represented by Formula I can be useful as anti-cancer agents.

These and other features of the present invention will become readily apparent upon further review of the following specification and drawings.

BRIEF DESCRIPTION OF THE DRAWINGS

The sole diagram is an exemplary reaction scheme for synthesis of an anti-cancer compound according to the present invention.

DETAILED DESCRIPTION OF THE PREFERRED EMBODIMENTS

The anti-cancer compounds include compounds represented by Formula I:

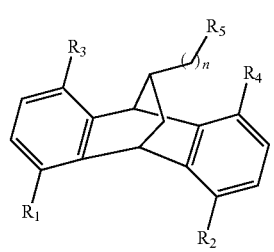

wherein $R_1$ and $R_2$ are either both hydrogen or both halogen, and if $R_1$ and $R_2$ are both hydrogen, $R_3$ and $R_4$ are both halogen, otherwise both $R_3$ and $R_4$ are hydrogen;

wherein $R_5$ is CHO or $NHCH_3$; and wherein n is 0 to 3;

provided that n is 0 only when $R_5$ is CHO, or a pharmaceutically acceptable salt or isomer thereof.

The anti-cancer compounds can be formulated as a pharmaceutical composition comprising the compound of Formula I and a pharmaceutically acceptable carrier.

According to an embodiment, the anti-cancer compounds can include compounds of Formula II:

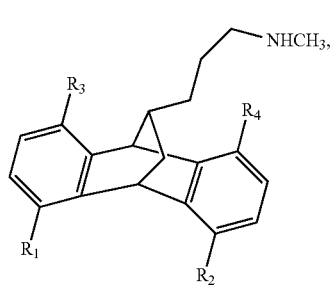

or a pharmaceutically acceptable salt or isomer thereof, wherein $R_1$ and $R_2$ are either both hydrogen or both halogen, and if $R_1$ and $R_2$ are both hydrogen, $R_3$ and $R_4$ are both halogen, otherwise both $R_3$ and $R_4$ are hydrogen.

According to an embodiment, the anti-cancer compound has the following structural formula:

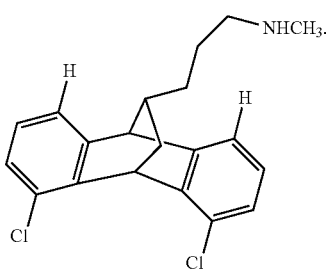 [SMILES: CNCCCC1CC2c3c(Cl)cccc3C1c1cccc(Cl)c12]

According to an embodiment, the anti-cancer compound has the following structural formula:

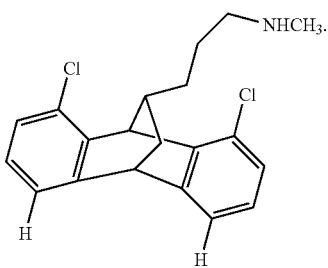 [SMILES: CNCCCC1CC2c3cccc(Cl)c3C1c1c(Cl)cccc12]

According to an embodiment, the anti-cancer compound has the following structural formula:

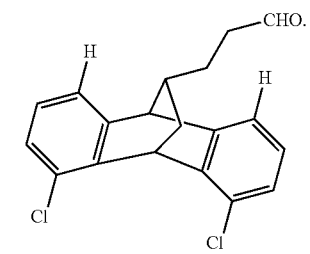 [SMILES: O=CCCC1CC2c3c(Cl)cccc3C1c1cccc(Cl)c12]

According to an embodiment, the anti-cancer compound has the following structural formula:

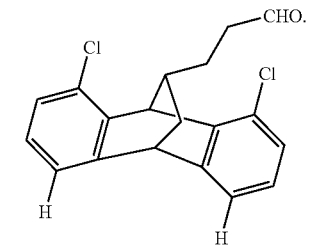 [SMILES: O=CCCC1CC2c3cccc(Cl)c3C1c1c(Cl)cccc12]

A method of making the anti-cancer compounds is exemplified herein by an example in which the halogen atoms are chlorine. However, it is believed that the same method may be employed for other halogens (bromine, fluorine, iodine), and that the final compounds have the same therapeutic effect as the dichloro examples described below.

The sole drawing FIGURE depicts a reaction scheme by which exemplary anti-cancer compounds can be prepared. Referring to the drawing FIGURE, the compounds can be prepared by: (a) reducing 1,8-dihaloanthrquinone 2 with zinc powder in aqueous ammonia, followed by acidic treatment to provide 1,8-dichloroanthracene 3; (b) Diels-Alder [4+2] cycloaddition reaction of the 1,8-dihaloanthracene 3 and acrolein at room temperature in the presence of boron trifluoride etherate to obtain a mixture of the intermediate compounds 4,5-dihalo-9,10-dihydo-9,10-ethanoanthracene-11-carbaldehyde 4 and 1,8-dihalo-9,10-dihydo-9,10-ethanoanthracene-11-carbaldehyde 5; (c) separating the mixture of carbaldehydes by column chromatography; and (d) direct reductive amination of the respective carbaldehydes to obtain the corresponding amines 6 and 7; (d) conversion of the aldehyde 5 into two, carbon homologated α,β unsaturated separable esters 8 and 9 by Wittig homologation using (carbethoxymethylene)triphenylphosphorane; (e) hydrogenation of the unsaturated esters 8 and 9 at room temperature in MeOH in the presence of Pd/C under $H_2$ (balloon) to obtain the saturated ester 10; (f) reduction of the ester with DIBAL (Diisobutylaluminium hydride) at room temperature to obtain the alcohol 11; (g) oxidation of the alcohol 11 using PCC (Pyridinium Chlorochromate) at room temperature in dichloromethane to obtain the aldehyde 12; (h) direct reductive amination of the aldehyde 12 was carried out by treating with 3 molar equivalents of a commercially available solution of methylamine in methanol in the presence of Pd—C as heterogeneous catalyst and stirred for 4 hours at room temperature under $H_2$ (balloon). After just filtration of the reaction mixture through a pad of celite and evaporation of the solvent, the corresponding amine 13 can be obtained.

The anti-cancer compounds can be used to treat cancer. As described in detail in the Examples below, the anti-cancer compounds exhibited potential anti-cancer activity when tested on cancer cell lines. In particular, in vitro anti-cancer activity was demonstrated by determining the $IC_{50}$ values in three carcinoma cell lines, including, the lung carcinoma cell line A549, the hepatocellular carcinoma HePG2 cell line, and the colorectal carcinoma HTC-116 cell line.

A pharmaceutically acceptable salt of the anti-cancer compound includes any non-toxic salt of the present anti-cancer compounds, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The anti-cancer compounds can be administered to a patient in need thereof. For example, the anti-cancer compounds can be used to treat a patient suffering from cancer, such as lung cancer, liver cancer, or colorectal cancer.

The anti-cancer compounds can be administered by any conventional route of administration, including, but not limited to, intravenous, oral, subcutaneous, intramuscular, intradermal and parenteral. Depending on the route of administration, the anti-cancer compounds can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an anti-cancer compound. To prepare the pharmaceutical composition, one or more anti-cancer compounds or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration; tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The anti-cancer compound can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The anti-cancer compound may also be coupled with soluble polymers as targetable drug carriers. Such polymers can include polyvinyl-pyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the anti-cancer compound may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation. The composition can be presented in a form suitable for daily, weekly or monthly administration. The pharmaceutical compositions herein will contain, per dosage unit, e.g., tablet, capsule, powder, injection, teaspoonful, suppository and the like, an amount of the active ingredient necessary to deliver an effective dose as described above.

The following examples will further illustrate the processes of synthesizing the chlorinated tetracyclic compounds of Formula 1 and the process described herein should be construed as exemplary only.

Example 1

Synthesis of 1,8-dichloroanthracene (3)

A suspension of 1,8-dichloroanthraquinone (2) (10.0 g, 36.1 mmol) and Zinc dust (50.0 g, 765 mmol) in (200 ml) of aqueous 28% $NH_3$ was stirred for 3 h at 100° C. After cooling to room temperature, the resulting solid was separated by suction filtration. A $CH_2Cl_2$ solution of the resulting crude solid was combined with the $CH_2Cl_2$ extract of the supernatant liquid, and the mixture was dried over $MgSO_4$ and concentrated under vacuo. The residual crude solid was dissolved in a mixture of (500 ml) of isopropanol and 50 ml of 12 M HCl and the resulting solution was refluxed for 3 h, then concentrated and partitioned between $CH_2Cl_2$ and 5% $NaHCO_3$. The organic layer was collected and dried over $MgSO_4$. The solvent was evaporated, and the crude solid product was recrystallized from a $CH_2Cl_2$-hexane mixture. The collected product was allowed to dry in the air for 24 h to provide (5.5 g., 62%) of 1,8-dichloroanthracene (3) as yellow needles: m.p. (153° C.) IR (KBr): $\nu$=1617, 1547, 1438, 1300, 1210, 953, 872, 775, 720, 678 $cm^{-1}$; $^1$H-NMR ($CDCl_3$, 400 MHz) $\delta$=7.25-7.88 (m; 6H, 8.36 (s; 1H, ArH-10), 9.16 (s; 1H, ArH-9) ppm; $^{13}$C NMR ($CDCl_3$, 100 MHz) $\delta$=120.9, 125.6, 126.0, 127.3, 127.6, 129.2, 132.4, 132.6 ppm; MS (EI) m/z (%)=246 (100) [M$^+$], 248 (65); HRMS (EI) Calcd. For $C_{14}H_8Cl_2$ [M$^+$] 246.0003, Found 246.0001.

Example 2

Synthesis of 4,5-dichloro-9,10-dihydro-9,10-ethanoanthracene-11-carbaldehyde (4) and 1,8-dichloro-9,10-dihydro-9,10-ethanoanthracene-11-carbaldehyde (5)

Acrolein (1.65 ml, 23.8 mmol) was added to a solution of 1,8-dichloroanthracene (3) (1.23 g, 5 mmol) in (70 ml) $CH_2Cl_2$, followed by dropwise addition of $BF_3.OEt_2$ (0.63 ml, 5 mmol). The mixture was stirred at room temperature for 3 h. During this time, the solution gradually turned brown, then the reaction was quenched with brine and extracted 3 times with $CH_2Cl_2$. The organic layer was collected and dried over $Na_2SO_4$, and the solvent was removed in vacuo. Column chromatography of the residue on silica gel (ethyl acetate/petroleum ether (1:10)) yields the aldehyde (4) ($R_f$=0.30) as colorless oil (0.15 g, 10%) and the aldehyde (5) ($R_f$=0.41) as colorless oil (1.0 g, 66%).

For compound (4), IR (KBr): $\nu$=2924, 1725, 1576, 1435, 1260, 1167, 1046, 770, 704 $cm^{-1}$; $^1$H NMR ($CDCl_3$, 400 MHz): $\delta$=2.01-2.04 (m; 1H, H-12), 2.10-2.12 (m; 1H, H-12), 2.81 (m; 1-H, H-11), 4.42 (t; J=2.64, 1H, H-9), 5.71 (d; J=2.5, 1H, H-10), 7.10-7.36 (m; 6H, ArH), 9.43 (d; J=1.7, 1H, CHO) ppm; $^{13}$C NMR ($CDCl_3$, 100 MHz): $\delta$=27.8, 37.8, 44.3, 50.6, 122.2, 126.7, 127.6, 127.9, 129.7, 136.2, 138.4, 145.7, 146.1, 200.7 ppm; MS (EI) m/z (%)=302 (20) [M⁺], 248 (85), 246 (100), 211 (5), 178 (4); HRMS (EI) Calcd. For $C_{17}H_{12}OCl_2$ [M⁺] 302.0265, Found 302.0266.

For compound (5), IR (KBr): ν=2944, 1727, 1577, 1455, 1210, 1167, 785, 770 cm⁻¹; ¹H NMR (CDCl₃, 400 MHz): δ=2.04-2.07 (m; 1H, H-12), 2.11-2.12 (m; 1-H, H-12), 2.79 (m; 1H, H-11), 4.75 (d; J=2.52, 1H, H-10), 5.48 (t; J=2.76, 1H, H-9), 7.04-7.28 (m; 6H, ArH), 9.46 (d; j=1.4, 1H, CHO) ppm; ¹³C NMR (CDCl₃, 100 MHz): δ=26.9, 36.6, 36.7, 45.5, 50.5, 122.1, 123.29, 127.1, 127.3, 129.7, 130.0, 141.5, 144.14, 201.7 ppm; MS (EI) m/z (%)=302 (20) [M⁺], 248 (75), 246 (100), 212 (8), 178(78); HRMS (EI) Calcd. For $C_{17}H_{12}OCl_2$ [M⁺] 302.0265, Found 302.0265.

Example 3

Synthesis of 1-(4,5-dichloro-9,10-dihydro-9,10-ethanoanthracen-11-yl)-N-methylmethanamine (6) and 1-(1,8-dichloro-9,10-dihydro-9,10-ethanoanthracen-11-yl)-N-methylmethanamine (7)

In a two-necked round-bottomed flask (40 mg of 10% Pd/C was wetted with methanol and the flask was evacuated, then flushed with hydrogen two times. A solution of (100 mg, 0.33 mmol) of aldehyde (4) (for synthesis of compound (6)) or aldehyde (5) (for synthesis of compound (7)) in (5 ml) methanol was then added to the reaction mixture, followed by the addition of (0.5 ml, 2 M) solution of methylamine in methanol. The mixture was stirred for 4 h at room temperature under H₂ atmosphere (balloon). The reaction mixture was filtered through a pad of celite, and the solvent was removed in vacuo to yield (90 mg., 85%) of the corresponding amine as white powder.

Compound (6) m.p. 290° C.; IR (KBr): ν=3440, 2942, 2864, 2775, 1592, 1457, 1410, 1026, 936, 755, 742, 555 cm⁻¹; ¹H NMR (CDCl₃, 400 MHz) δ=1.27-1.37 (m; 1H, H-12), 2.13-2.19 (m; 1H, H-12), 2.47-2.50 (m; 1H-H-11), 2.55-2.66 (m; 5H-CH₂—N—CH₃), 4.31 (t; J=2.52, 1H, H-9), 4.63 (d; J=2.04, 1H, H-10), 6.98-7.05 (m; 3H, ArH), 7.17-7.19 (m; 2H, ArH), 7.45-7.48 (m; 1H, ArH) ppm; ¹³C NMR (CDCl₃, 125 MHz) δ=33.2, 33.9, 35.9, 43.7, 46.0, 54.7, 123.3, 123.5, 123.8, 125.6, 125.9, 126.0, 126.4, 139.3, 142.7, 142.9, 143.5 ppm. MS (EI): m/z (%)=317 ([M+], not recorded), 306 (7), 305 (22), 251 (75), 250 (100), 220 (7), 219 (22), 179 (5), 179 (4), 178 (13), 111 (8).

Compound (7) m.p. 310° C.; IR (KBr): ν=3435, 2943, 2774, 1626, 1593, 1457, 1411, 1027, 937, 758, 742, 555 cm⁻¹; ¹H NMR (CDCl₃, 500 MHz) δ=1.24-1.26 (m; 1H, H-12), 2.04-2.08 (m; 1H, H-12), 2.38-2.40 (m; H-1, H-11), 2.45-2.54 (m; 5H-CH₂—N—CH₃), 4.21 (broad s; 1H, H-10), 4.52 (broad s; 1H, H-9), 6.98-7.05 (m; 3H, ArH), 7.17-7.19 (m; 2H, ArH), 7.42-7.43 (m; 1H, ArH) ppm; ¹³C NMR (CDCl₃, 125 MHz) δ=33.1, 33.6, 35.5, 43.5, 45.8, 54.3, 123.4, 123.5, 123.8, 125.6, 126.0, 126.1, 126.5, 139.1, 142.4, 142.8, 143.4 ppm; MS (EI) m/z (%)=318 (100) [M⁺], 284 (22), 186(15), 117 (53); HRMS (EI) Calcd. for $C_{18}H_{18}NCl_2$ [M⁺] 318.0816, Found 318.0809.

Example 4

Synthesis of Z-ethyl 3-(1,8-dichloro-9,10-dihydro-9,10-ethanoanthracen-11-yl)propenoate (8) and E-ethyl 3-(1,8-dichloro-9,10-dihydro-9,10-ethanoanthracen-11-yl)propenoate (9)

(Carbethoxymethylene)triphenylphosphorane (2 g, 5.75 mmol) was added to a solution of the aldehyde (5) (1.2 g, 4 mmol) in (36 ml) CH₂Cl₂. The reaction mixture was stirred at room temperature for 5 h. The solvent was removed and the residue was purified via flash column chromatography on silica gel using (Ethyl acetate A/Petroleum ether, 1:5) to afford separable isomers (8) and (9) (1.45 g, 97%) in ratio of 1:2 respectively as yellow oil.

Compound (8) IR (KBr): ν=3066, 2927, 2860, 1716, 1641, 1575, 1456, 1190, 1029, 771, 759, 594 cm⁻¹; ¹H NMR (CDCl₃, 400 MHz): δ=1.20 (t; J=7.3, 314, —O—CH₂—CH₃), 1.24-1.29 (m; 1H, H-12) 2.11-2.14 (m; 1H, H-12), 3.76 (m; 1H, H-11), 4.08 (q; J=7.3, 2H, —O—CH₂—CH₃), 4.18 (d; J=2.9, 1H, H-10), 5.29 (t; J=2.9, H-1, H-9), 5.47 (dd; J=11.3, 9.5, 1H, —CH=CH—COO—), 5.61 (d; J=11.7, 1H, —CH=CH—COO—), 6.96-7.19 (m; 6H, ArH) ppm; ¹³C NMR (CDCl₃, 100 MHz): δ=14.2, 33.1, 36.5, 36.9, 49.7, 60.0, 119.6, 122.1, 123.7, 126.6, 126.8, 127.0, 129.3, 129.5, 139.5, 140.3, 142.3, 145.2, 152.2, 166.0 ppm; MS (EI): m/z (%)=372 (10) [M⁺], 367 (5), 248 (65), 246 (100), 176 (18), 131 (5), 69 (12); HRMS (EI): Calcd. For $C_{21}H_{18}O_2Cl_2$ [M⁺] 372.0684, Found 372.0683.

Compound (9) IR (KBr): ν=3066, 2979, 2935, 2898, 1718, 1650, 1577, 1456, 1446, 1369, 1271, 1180, 1039, 985, 769, 740, 703, 590 cm⁻¹; ¹H NMR (CDCl₃, 400 MHz): δ=1.22 (t; J=7.3, 3H, —O—CH₂—CH₃), 1.22-1.24 (m; 1H, H-12) 2.04-2.07 (m; 1H, H-12), 2.71 (m; 1H, H-11), 4.12 (q; J=7.3, 2H, —O—CH₂—CH₃), 4.20 (d; J=2.2, 1H, H-10), 5.35 (t; J=2.5, H-1, H-9), 5.75 (d; J=15.4, 1H, —CH=CH—COO—), 6.36 (dd; J=15.4; 9.5, 1H, —CH=CH—COO—), 7.04-7.24 (m; 6H, ArH) ppm; ¹³C NMR (CDCl₃, 100 MHz): δ=14.2, 32.0, 36.8, 40.9, 49.7, 60.3, 121.5, 121.9, 123.8, 126.7, 126.9, 127.0, 127.1, 129.3, 129.8, 139.5, 140.2, 141.6, 145.1, 150.5, 166.2 ppm; MS (EI): m/z (%)=372 (41) [M⁺], 367 (19), 248 (62), 246 (100), 176 (29); HRMS (EI): Calcd. For $C_{21}H_{18}O_2Cl_2$ [M⁺] 372.0684, Found 372.0683.

Example 5

Synthesis of ethyl 3-(1,8-dichloro-9,10-dihydro-9,10-ethanoanthracen-11-yl)propanoate (10)

In a two-necked round-bottomed flask, 0.37 g of 10% Pd/C was wetted with ethanol and the flask was evacuated, and flushed with hydrogen two times, then solution of (1.3 g, 3.5 mmol) unsaturated ester (8) and (9) in (40 ml) ethanol was added to the reaction mixture. The mixture was stirred for 24 h at room temperature under H₂ (balloon). The reaction mixture was filtered through a pad of celite and the solvent was removed in vacuo to afford the corresponding (10) 1.2 g, 92% as yellow oil.

IR (KBr): ν=3020, 2933, 2900, 1733, 1460, 1375, 1261, 1176, 1029, 754, 559 cm⁻¹; ¹HNMR (CDCl₃, 400 MHz): δ=1.12-1.16 (m; 2H, H-¹1), 1.24 (t; J=7.3, 3H, —O—CH₂—CH₃), 1.46-1.51 (m; 1H, H-12), 1.86-1.93 (m; 1H, H-11), 1.97-2.04 (m; 1H, H-12), 2.31 (t; J=8.0, 2H, H-²2), 4.08 (q; J=7.3, 2H, —O—CH₂—CH₃), 4.15 (d; J=2.2, 1H, H-10), 5.29 (t; J=2.5, 1H, H-9), 6.99-7.25 (m; 6H, ArH) ppm; ¹³C NMR (CDCl₃, 100 MHz): δ=14.1, 31.1, 32.4, 34.3, 37.9, 44.1, 48.7, 60.2, 122.9, 123.2, 123.3, 125.2, 125.4, 125.5, 125.5, 125.8, 140.4, 143.2, 143.7, 144.2, 173.4 ppm; MS (EI): m/z (%)=374 ([M⁺], not recorded), 331 (11), 329 (25), 295 (12), 248 (58), 246 (100), 212 (46), 178 (45).

Example 6

Synthesis of 3-(1,8-dichloro-9,10-dihydro-9,10-ethanoanthracen-11-yl)propan-1-ol (11)

To a solution of saturated ester (10), 600 mg, 1.6 mmol in CH₂Cl₂ (6 ml), DIBAL (7 ml) was added. The reaction mixture was stirred for 5 h at room temperature. Then the reaction mixture was quenched with Methanol (1 ml) followed by the addition of ethyl acetate (30 ml) and saturated aqueous of NH$_4$Cl (10 ml). The quenched reaction mixture was filtered through suction funnel and extracted with CH$_2$Cl$_2$ and the combined organic layers were washed with brine, dried over MgSO$_4$, filtered, and concentrated in vacuo. The residue was purified via flash column chromatography on silica gel using ethyl acetate/hexane (1:3) to afford (11) (280 mg, 53%) as a milky viscous oil.

IR (KBr): ν=3577, 3336, 2970, 2933, 2860, 1456, 1055, 756, 567 cm$^{-1}$; $^1$HNMR (CDCl$_3$, 400 MHz): δ=0.87-0.98 (m; 2H, H-′1), 1.13-1.28 (m; 1H, H-12), 1.53-1.63 (m; 1H, H-11), 1.84-1.93 (m; 2H, H-′2), 1.97-2.08 (m; 1H, H-12), 3.47 (t; J=6.6, 2H, —CH$_2$OH), 4.04 (d; J=2.2, 1H, H-10), 4.16 (t; J=2.5, 1H, H-9), 7.01-7.17 (m; 6H, ArH) ppm; $^{13}$C NMR (CDCl$_3$, 100 MHz): δ=30.6, 32.2, 34.6, 38.2, 44.3, 48.9, 62.8, 122.9, 123.1, 123.3, 125.2, 125.3, 125.4, 125.5, 125.6, 140.7, 143.3, 143.8, 144.4 ppm; MS (EI): m/z (%)=332 ([M$^+$], not recorded), 295 (7), 264 (12), 212 (29), 178 (100), 1152 (4).

Example 7

Synthesis of 3-(1,8-dichloro-9,10-dihydro-9,10-ethanoanthracen-11-yl)propanal (12)

To a solution of alcohol (11) (250 mg, 0.75 mmol) in CH$_2$Cl$_2$ (6 ml), PCC (250 mg, 1.2 mmol) was added. The reaction mixture was stirred for 2 h at room temperature. The reaction mixture was concentrated in vacuo and the residue was purified via flash column chromatography on silica gel using ethyl acetate/hexane (1:3) to afford (12) (250 mg, 100%) as a colorless oil.

IR (KBr): ν=3020, 2935, 2862, 2812, 1726, 1460, 1172, 1026, 760, 754, 559 cm$^{-1}$; $^1$HNMR (CDCl$_3$, 400 MHz): δ=1.12-1.25 (m; 2H, H-′1), 1.43-1.50 (m; 1H, H-12), 1.84-1.90 (m; 1H, H-11), 1.97-2.04 (m; 1H, H-12), 2.41-2.45 (m, 2H, H-′2), 4.10 (d; J=2.2, 1H, H-10), 4.25 (t; J=2.9, 1H, H-9), 7.09-7.25 (m; 6H, ArH), 9.69 (t; J=1.4, 1H, CHO) ppm; $^{13}$C NMR (CDCl$_3$, 100 MHz): δ=28.3, 34.5, 37.9, 41.9, 44.1, 48.7, 123.0, 123.2, 123.4, 125.6, 125.5, 125.6, 125.6, 125.9, 140.2, 143.1, 143.7, 144.0, 202.1 ppm; MS (EI): m/z (%)=330 ([M+], not recorded), 321 (7), 319 (11), 311 (12), 289 (7), 251 (6), 225 (8), 204 (11), 201 (21), 199 (51), 197 (92), 181 (28), 165 (100), 151 (38), 149 (15).

Example 8

Synthesis of 3-(1,8-dichloro-9,10-dihydro-9,10-ethanoanthracen-11-yl)-N-methylpropan-1-amine (13)

In a two-necked round-bottom flask (100 mg, 10% Pd/C) was wetted with dichloromethane and the flask was evacuated, flushed with hydrogen two times, then a solution of (110 mg, 0.33 mmol) aldehyde (12) in (5 ml) methanol was added to the reaction mixture followed by the addition of (0.7 ml, 2M) solution of methylamine in methanol. The mixture was stirred for 4 h at room temperature under H$_2$ (balloon). The reaction mixture was filtered through a pad of celite and the solvent was removed in vacuo to yield (90 mg, 79%) of the corresponding amine (13) as white powder.

m.p. 178° C.; IR (KBr): ν=3414, 2935, 2864, 1471, 1399, 1171, 1034, 804, 752, 551, 466 cm$^{-1}$; $^1$HNMR (CDCl$_3$, 400 MHz): δ=0.79-0.87 (m; 2H, H-′1), 1.0-1.10 (m; 2H, H-′2), 1.2 (s; 3H, N—CH$_3$), 1.73-1.79 (m; 1H, H-11), 1.85-1.92 (m; 2H, H-12), 2.68-2.72 (m; 2H, H-′3), 3.18 (d; J=1.8, 3H, N—CH$_3$), 4.03 (d; J=2.2, 1H, H-10), 4.13 (t; J=2.2, 1H, H-9), 6.97-7.02 (m; 3H, ArH), 7.13-7.18 (m; 3H, ArH) ppm; $^{13}$C NMR (CDCl$_3$, 100 MHz): δ=23.8, 32.8, 32.9, 34.4, 37.7, 44.1, 48.5, 49.2, 122.9, 123.3 (2×), 125.2, 125.4, 125.5, 125.6, 125.8, 140.3, 143.2, 143.6, 144.0 ppm; MS (EI): m/z (%)=346 (18) [M$^+$+H], 336 (19), 335 (31), 334 (75), 332 (100), 326 (5), 318 (11), 298 (11), 286 (5), 284 (9); HRMS (EI): Calcd. For C$_{20}$H$_{22}$NCl$_2$ [M$^+$] 346.1129, Found 346.1128.

Example 9

Anti-Cancer Activity Evaluation

In vitro anti-cancer activity was demonstrated by determining the IC$_{50}$ values in three cancer cell lines, including the lung carcinoma cell line A549, the hepatocellular carcinoma HepG2 cell line, and the colorectal carcinoma HTC-116 cell line (Table 1). Growth inhibitions were measured in 96-well plates. Aliquots of 120 μL of the suspended cells (50,000 mL$^{-1}$) were given to 60 μL of a serial dilution of the inhibitor (S). After 5 days of incubations, growths were determined the MTT assay (MTT=3-(4,5-dimethylthiazol-2-yl)-2,5-diphenyltetrazolium bromide). Briefly, 20 μl MTT (5 mg/mL in PBS) were added to each well, and the plates were incubated for 2 h at 37° C., and 5% CO$_2$-atmosphere in the cell incubator. The supernatants were then discarded and 200 μl of isopropanol/HCl were added to each well and mixed to dissolve the formazan crystals. The absorbance was then read at 550 nm using a microplate reader (Thermo Scientific, USA). The viability of the cells was calculated by dividing the absorbance average of the treated cells by the absorbance average of the control cells multiply 100%. The IC$_{50}$ values were defined as sample concentration inhibiting 50% of cell growth. The activities of the cells were plotted against the concentration of the drugs, and the IC$_{50}$ values were calculated from the regression curve.

TABLE 1

Cancer Cell Lines

| No. | Cell line | ATCC-No. | Disease or organ |
|---|---|---|---|
| 1 | A549 | A549 (ATCC ® CCL-185 ™) | Lung Carcinoma |
| 2 | HepG2 | HepG2 [HEPG2] (ATCC ® HB-8065 ™) | Hepatocellular carcinoma |
| 3 | HTC-116 | HCT 116 (ATCC ® CCL-247 ™) | Colorectal Carcinoma |

The cancer cell lines were incubated with serial dilution of each compound (from 313 pg ML$^{-1}$ to 5 mg ML$^{-1}$) in a 96-well plate for 4 days, and then tested for growth inhibition by MTT-Test. Maprotiline had been used as a positive control. The results showed that all tested derivatives were able to inhibit the growths of the cancer cell lines A549 as well as HePG2 at low micromolar concentrations. In addition, compound 4 and compound 5 were also able to inhibit the growth of a third cell line (HCT). The calculated IC$_{50}$ values of all compounds, and that from maprotiline, are given in Table 2. Additionally, the tested cancer cell lines showed the highest sensitivity to the compounds 4 and 5. Replacing the formyl groups of the two compounds with amino groups (Sub. 6 and Sub. 7) caused remarkable decreasing of cells sensitivities, and accordingly increasing of IC$_{50}$ values of the two derivatives as shown in table 2. This result suggests a direct or an indirect role of the formyl group in the biological activity of the two derivatives. Moreover, the sensitivities of the treated cancer cells to 4 and 5 were 6 times higher in case of the breast cancer cell line A459, and even 40 times higher in case of hepatocyte carcinoma cell line HepG2.

TABLE 2

The IC$_{50}$ of the Tested Compounds

| Substance | A549 IC$_{50}$ value µg/ml | HepG2 IC$_{50}$ value µg/ml | HCT IC$_{50}$ value µg/ml |
|---|---|---|---|
| 4 | 1.1 (0.2)± | 0.12 (±0.03) | 0.4 (±0.1) |
| 5 | 3.71 (±0.8) | 0.65 (±0.1) | 0.7 (±0.1) |
| 7 | 18.9 (±2.5) | 13.8 (±0.6) | ND |
| 6 | 25.5 (±5.2) | 12.66 (±4.4) | ND |
| 13 | 7.8 (±1.25) | 4.44 (±0.41) | ND |
| Maprotiline | 6.1 (±1.16) | 5.15 (±0.77) | ND |

ND = Not determined

The anti-cancer compounds of Formula I are useful particularly as anti-cancer agents as well as new intermediates. These compounds also have potential use as antidepressant or lead compounds.

It is to be understood that the present invention is not limited to the embodiments described above, but encompasses any and all embodiments within the scope of the following claims.

We claim:

1. An anti-cancer compound having the formula:

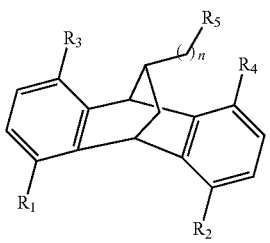

wherein $R_1$ and $R_2$ are either both hydrogen or both halogen, and if $R_1$ and $R_2$ are both hydrogen, $R_3$ and $R_4$ are both halogen, otherwise both $R_3$ and $R_4$ are hydrogen;
wherein $R_5$ is CHO or NHCH$_3$; and
wherein n is 0 to 3;
provided that n is 0 only when $R_5$ is CHO,
or a pharmaceutically acceptable salt thereof.

2. The anti-cancer compound according to claim 1, wherein $R_1$ and $R_2$ are both hydrogen, $R_3$ and $R_4$ are both halogen, n is 3, and $R_5$ is NHCH$_3$.

3. The anti-cancer compound according to claim 1, wherein $R_1$ and $R_2$ are both hydrogen, $R_3$ and $R_4$ are both chlorine, n is 3, and $R_5$ is NHCH$_3$.

4. The anti-cancer compound according to claim 1, wherein $R_3$ and $R_4$ are both hydrogen, $R_1$ and $R_2$ are both halogen, n is 3, and $R_5$ is NHCH$_3$.

5. The anti-cancer compound according to claim 1, wherein $R_3$ and $R_4$ are both hydrogen, $R_1$ and $R_2$ are both chlorine, n is 3, and $R_5$ is NHCH$_3$.

6. A pharmaceutical composition, comprising an anti-cancer compound according to claim 1 and a pharmaceutically acceptable carrier.

7. The pharmaceutical composition according to claim 6, wherein the anti-cancer compound has the formula:

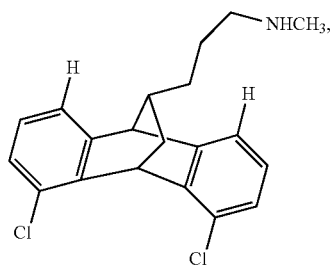 [SMILES: CNCCCC1CC2c3c(Cl)cccc3C1c1cccc(Cl)c12]

or a pharmaceutically acceptable salt thereof.

8. The pharmaceutical composition according to claim 6, wherein the anti-cancer compound has the formula:

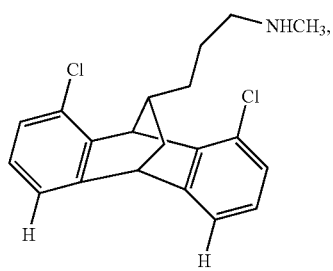 [SMILES: CNCCCC1CC2c3cccc(Cl)c3C1c1c(Cl)cccc12]

or a pharmaceutically acceptable salt thereof.

9. A method for treating cancer, comprising the step of administering to a patient a therapeutically effective amount of the pharmaceutical composition according to claim 6.

10. A method of preparing an anti-cancer compound, comprising the steps of:
   (a) reducing 1,8-dihaloanthraquinone with zinc powder in aqueous ammonia, followed by acidic treatment to provide 1,8-dihaloanthracene;
   (b) performing a Diels-Alder [4+2] cycloaddition reaction of the 1,8-dihaloanthracene and acrolein at room temperature in the presence of boron trifluoride etherate to obtain a mixture of the intermediate compounds 1,8-dihalo-9,10-dihydro-9,10-ethanoanthracene-11-carbaldehyde and 4,5-dihalo-9,10-dihydro-9,10-ethanoanthracene 11-carbaldehyde;
   (c) separating the mixture of carbaldehydes by column chromatography;
   (d) converting the 4,5-dihalo-9,10-dihydro-9,10-ethanoanthracene 11-carbaldehyde into Z-ethyl 3-(1,8-dihalo-9,10-dihydro-9,10-ethanoanthracen-11-yl)propenoate and E-ethyl 3-(1,8-dihalo-9,10-dihydro-9,10-ethanoanthracen-11-yl)propenoate by Wittig homologation using (carbethoxymethylene)triphenylphosphorane;
   (e) hydrogenating Z-ethyl 3-(1,8-dihalo-9,10-dihydro-9,10-ethanoanthracen-11-yl)propenoate and E-ethyl 3-(1,8-dihalo-9,10-dihydro-9,10-ethanoanthracen-11-yl) propenoate at room temperature in methanol in the presence of palladium catalyst under hydrogen to obtain ethyl 3-(1,8-dihalo-9,10-dihydro-9,10-ethanoanthracen-11-yl)propanoate;
   (f) reducing ethyl 3-(1,8-dihalo-9,10-dihydro-9,10-ethanoanthracen-11-yl)propanoate with DIBAL at room temperature to obtain 3-(1,8-dihalo-9,10-dihydro-9,10-ethanoanthracen-11-yl)propan-1-ol;
   (g) oxidizing 3-(1,8-dihalo-9,10-dihydro-9,10-ethanoanthracen-11-yl)propan-1-ol using PCC at room temperature in dichloromethane to obtain 3-(1,8-dihalo-9,10-dihydro-9,10-ethanoanthracen-11-yl)propanal; and
(h) aminating the 3-(1,8-dihalo-9,10-dihydro-9,10-ethanoanthracen-11-yl)propanal by direct reductive amination to obtain the anti-cancer compound of the formula
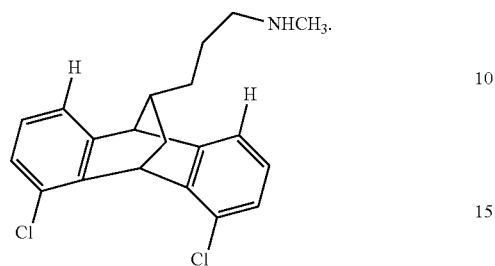
* * * * *